(12) United States Patent
Parker (10) Patent No.: US 7,763,066 B2
(45) Date of Patent: Jul. 27, 2010

(54) STENT WITH AN END MEMBER HAVING A LATERAL EXTENSION

(75) Inventor: Fred T. Parker, Unionville, IN (US)

(73) Assignee: Cook Incorporated, Bloomington, IN (US)

( * ) Notice: Subject to any disclaimer, the term of this patent is extended or adjusted under 35 U.S.C. 154(b) by 1301 days.

(21) Appl. No.: 10/900,516

(22) Filed: Jul. 28, 2004

(65) Prior Publication Data
US 2006/0025847 A1 Feb. 2, 2006

(51) Int. Cl.
*A61F 2/06* (2006.01)
(52) U.S. Cl. .............. 623/1.15; 623/1.31; 623/1.34; 606/200
(58) Field of Classification Search ............ 623/1.11, 623/1.15, 1.2, 1.1, 1.46, 1.14, 1.16; 606/194, 606/108, 198; 604/21, 501, 104, 105, 107
See application file for complete search history.

(56) References Cited

U.S. PATENT DOCUMENTS

| 5,507,771 | A | | 4/1996 | Gianturco |
| 5,591,197 | A | * | 1/1997 | Orth et al. ............. 623/1.16 |
| 5,810,872 | A | | 9/1998 | Kanesaka et al. |
| 5,861,027 | A | * | 1/1999 | Trapp ................. 623/1.15 |
| 5,922,020 | A | | 7/1999 | Klein et al. |
| 6,231,598 | B1 | | 5/2001 | Berry et al. |
| 6,273,909 | B1 | | 8/2001 | Kugler et al. |
| 6,280,466 | B1 | | 8/2001 | Kugler |
| 6,293,966 | B1 | | 9/2001 | Frantzen ............. 623/1.15 |
| 6,312,459 | B1 | | 11/2001 | Huang et al. |
| 6,331,190 | B1 | | 12/2001 | Shokoohi et al. |
| 6,464,720 | B2 | * | 10/2002 | Boatman et al. ......... 623/1.15 |
| 7,243,408 | B2 | * | 7/2007 | Vietmeier .............. 29/447 |
| 2001/0027339 | A1 | | 10/2001 | Boatman et al. |
| 2004/0015229 | A1 | * | 1/2004 | Fulkerson et al. ........ 623/1.22 |
| 2004/0044401 | A1 | * | 3/2004 | Bales et al. ............. 623/1.22 |

FOREIGN PATENT DOCUMENTS

| DE | 203 18 351 U1 | * | 8/2003 |
| DE | 203 18 351 U1 | | 2/2004 |
| EP | 1 157 673 A2 | | 11/2001 |

OTHER PUBLICATIONS

International Search Report from corresponding PCT application No. PCT/US2005/025825 dated Nov. 10, 2005, 7 pages.

* cited by examiner

*Primary Examiner*—Gary Jackson
*Assistant Examiner*—Julie A Szpira
(74) *Attorney, Agent, or Firm*—Brinks Hofer Gilson & Lione (57) ABSTRACT

A marker and pushing member are provided with lateral extensions connected to a connecting portion. The connecting portion connects the marker/pushing member to a proximal or distal end of the stent. The lateral extensions distribute forces applied to the marker/pushing member so that part of the force is applied to the connecting member and part of the force is applied to a portion of the stent structure that is not directly connected to the connecting member.

18 Claims, 4 Drawing Sheets

STENT WITH AN END MEMBER HAVING A LATERAL EXTENSION

BACKGROUND

The present invention relates generally to medical devices and particularly to a stent with a pushing member at the proximal or distal end of the stent.

The use of stents to treat various organs, such as the vascular system, colon, biliary tract, urinary tract, esophagus, trachea and the like, has become common in recent years. Stents are most commonly used to treat blockages, occlusions, narrowing ailments and other similar problems that restrict flow through a passageway. One area where stents are now commonly used for treatment involves implanting an endovascular stent into the vascular system in order to improve or maintain blood flow through narrowed arteries. Stents have been shown to be useful in treating various vessels throughout the vascular system, including both coronary vessels and peripheral vessels (e.g., carotid, brachial, renal, iliac and femoral).

The use of stents in coronary vessels has drawn particular attention from the medical community because of the growing number of people each year that suffer from heart problems associated with stenosis (i.e., narrowing of a vessel). This has led to an increased demand for medical procedures to treat such problems. The widespread frequency of heart problems may be due to a number of societal changes, including the tendency of people to exercise less and the prevalence of unhealthy diets, in conjunction with the fact that people generally have longer life spans now than previous generations. Stents have become a popular alternative for treating coronary stenosis because stenting procedures are considerably less invasive than conventional procedures. Traditionally, stenosis of the coronary arteries has been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient. To address the growing demand for non-invasive medical procedures for the treatment of coronary vessels and other passageway problems, the medical community has begun to turn away from conventional invasive procedures like bypass surgery and increasingly the treatment of choice now involves various types of stenting procedures.

Many different types of stents and stenting procedures are possible. In general, however, stents are typically designed as tubular support structures that may be inserted percutaneously and transluminally through a body passageway. Traditionally, stents are made from a metal or other synthetic material with a series of radial openings extending through the support structure of the stent to facilitate compression and expansion of the stent. Although stents may be made from many types of materials, including non-metallic materials, common examples of metallic materials that may be used to make stents include stainless steel, nitinol, cobalt-chrome alloys, amorphous metals, tantalum, platinum, gold and titanium. Typically, stents are implanted within a passageway by positioning the stent within the area to be treated and then expanding the stent from a compressed diameter to an expanded diameter. The ability of the stent to expand from a compressed diameter makes it possible to thread the stent to the area to be treated through various narrow body passageways while the stent is in the compressed diameter. Once the stent has been positioned and expanded at the area to be treated, the tubular support structure of the stent contacts and radially supports the inner wall of the passageway. As a result, the implanted stent mechanically prevents the passageway from closing and keeps the passageway open to facilitate fluid flow through the passageway.

Stents can generally be characterized as either balloon-expandable or self-expandable. However, stent designs and implantation procedures vary widely. For example, although physicians often prefer particular types of stents for certain types of procedures, the uses for balloon-expandable and self-expandable stents frequently overlap and procedures related to one type of stent are frequently adapted to other types of stents.

Balloon-expandable stents are generally used to treat stenosis of the coronary arteries. Usually, balloon-expandable stents are made from ductile materials that plastically deform relatively easily. In the case of stents made from metal, 316L stainless steel that has been annealed is a common choice for this type of stent. One procedure for implanting balloon-expandable stents involves mounting the stent circumferentially on the balloon of a balloon-tipped catheter and threading the catheter through a vessel passageway to the area to be treated. Once the balloon is positioned at the narrowed portion of the vessel to be treated, the balloon is expanded by pumping saline through the catheter to the balloon. The balloon then simultaneously dilates the vessel and radially expands the stent within the dilated portion. The balloon is then deflated and the balloon-tipped catheter is retracted from the passageway. This leaves the expanded stent permanently implanted at the desired location. Ductile metal lends itself to this type of stent since the stent may be compressed by plastic deformation to a small diameter when mounted onto the balloon. When the balloon is then expanded in the vessel, the stent is once again plastically deformed to a larger diameter to provide the desired radial support structure. Traditionally, balloon-expandable stents have been more commonly used in coronary vessels than in peripheral vessels because of the deformable nature of these stents. One reason for this is that peripheral vessels tend to experience frequent traumas from external sources (e.g., impacts to a person's arms, legs, etc.) which are transmitted through the body's tissues to the vessel. In the case of peripheral vessels, there is an increased risk that an external trauma could cause a balloon-expandable stent to once again plastically deform in unexpected ways with potentially severe and/or catastrophic results. In the case of coronary vessels, however, this risk is minimal since coronary vessels rarely experience traumas transmitted from external sources.

Self-expandable stents are increasingly used and accepted by physicians for treating a variety of ailments. Self-expandable stents are usually made of shape memory materials or materials that act like a spring. Typical metals used in this type of stent include nitinol and 304 stainless steel. A common procedure for implanting a self-expandable stent involves a two-step process. First, the narrowed vessel portion to be treated is dilated with a balloon as described above. Second, the stent is implanted into the dilated vessel portion. To facilitate stent implantation, the stent is installed on the end of a catheter in a compressed, small diameter state and is usually retained in the small diameter by inserting the stent into a sheath at the end of the catheter. The stent is then guided to the balloon-dilated portion and is released from the catheter by pulling the retaining sheath off the stent. Once released from the retaining sheath, the stent radially springs outward to an expanded diameter until the stent contacts and presses against the vessel wall. Traditionally, self-expandable stents have been more commonly used in peripheral vessels than in coronary vessels due to the shape memory characteristic of the metals that are used in these stents. One advantage of self-expandable stents for peripheral vessels is that traumas from external sources do not permanently deform the stent. Instead, the stent may temporarily deform during an unusually harsh trauma but will spring back to its expanded state once the trauma is relieved. Self-expandable stents, however, are often considered to be less preferred for coronary vessels as compared to balloon-expandable stents. One reason for this is that balloon-expandable stents can be precisely sized to a particular vessel diameter and shape since the ductile metal that is used can be plastically deformed to a desired size and shape. In contrast, self-expandable stents are designed with a particular expansible range. Thus, after being implanted, self-expandable stents continue to exert pressure against the vessel wall.

Typically, stents are provided with markers and/or pushing members that are attached or formed along the proximal and/or distal ends of the stent structure. These features may be used for a number of purposes and usually serve more than one function. For example, markers are usually provided at both the proximal and distal ends of the stent to assist the physician in positioning the stent during stenting procedures. Generally, separate markers are needed on most stents since the stent structure itself cannot usually be seen easily on x-ray and other visualization equipment. This is due in part to the types of material that are usually used in stent structures and the slenderness of the structural members in the stent structure. Markers address this visualization problem by providing features with increased radiopacity along the proximal and distal ends of the stent. The features (i.e., the markers) are typically larger in width than the structural members of the stent structure and usually are filled with a radiopaque material like gold or platinum. As a result, the radiopaque material in the markers can be seen more easily on the physician's visualization equipment than the stent structure itself.

Pushing members are also used at the proximal and/or distal ends of many stents. Pushing members are particularly useful for self-expandable stents but may also be used on balloon-expandable stents. In either case, the pushing members provide a separate contact surface at the end of the stent that may be pushed against. As a result, the stent structure itself is not directly pushed against. In the case of self-expandable stents, the pushing members of the stent are used at several different times. For example, during the manufacture of self-expandable stents and their corresponding delivery systems, the stent must be loaded into the delivery system in a compressed state. Delivery systems for self-expandable stents are well known to those in the art, and therefore, a detailed description is not necessary. However, as described above, delivery systems for self-expandable stents usually include a retaining sleeve at the end of a catheter which restrains the outer surface of the stent and keeps the stent compressed until the stent is released at the site of implantation. A common manufacturing method for loading stents into the retaining sleeve involves compressing the stent while at the same time pushing on one end of the stent in order to slide the stent into the sleeve. Alternatively, the stent may be compressed and pushed into a transfer tube first and then pushed again through the transfer tube into the delivery system.

Pushing members are also used on the proximal end of self-expandable stents in order to release the stent from the delivery system for implantation. As previously described, self-expandable stents are released for implantation by pulling the retaining sleeve off the stent. Typically, the delivery system also includes a holder within the retaining sleeve which contacts the proximal end of the stent. Generally, the holder and the sleeve are designed to move relative to each other so that as the sleeve is pulled back, the holder can be maintained in place. As a result, the holder prevents the stent from moving rearward with the retaining sleeve as the sleeve is pulled back. In effect, the stent is pushed out of the sleeve by the holder as the sleeve is pulled rearward.

Typically, the markers on a stent are also used as pushing members and vice versa. One problem with current stent structures is that the pushing force that is transmitted by the pushing member to the stent structure is concentrated onto a small number of structural members in the stent structure. As a result, the pushing force can cause the structural members to bend and deform as the stent is being pushed. In extreme cases, this concentrated force can permanently deform parts of the stent structure. This problem is of particular concern on longer length stents. Generally, most stents that are currently used for medical treatments are 8 cm or less in length. However, stents that are longer than 8 cm are becoming more common to treat various peripheral arteries, such as the superficial femoral artery. When longer stents like these are pushed, either during loading into the delivery system or during release, higher frictional forces must be overcome in order to move the stent. The longer length of some of these stents also makes the stents generally less stable than shorter stents. As a result, the bending and deforming problems that may occur when pushing on a stent tend to be more pronounced and damaging on longer stents. However, these types of problems may exist with all stents. Because most pushing members are also used as markers, it has been difficult to identify solutions that minimize these types of bending problems while also providing an acceptable structural member for visualization. Moreover, the pushing members must not interfere with compression and expansion of the stent, which has also limited the alternatives available.

Accordingly, it is apparent to the inventor that an improved marker and/or pushing member is desired for the proximal and distal ends of a stent. A solution to these and other problems is described more fully below.

BRIEF SUMMARY

A marker and pushing member are provided which distribute pushing forces more evenly to the stent structure. As a result, bending and deformation of the stent structure that may occur when pushing forces are applied to the ends of the stent are minimized. In the described embodiments, the marker has lateral extensions attached to or formed onto the connecting portion of the marker that connects the marker to the stent structure. The lateral extensions distribute some of the forces to structural members of the stent structure which are not directly connected to the connecting portion. Thus, unlike prior art markers that are used as pushing members, the entire pushing force is not concentrated on only the structural members that are directly connected to the connecting portion.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
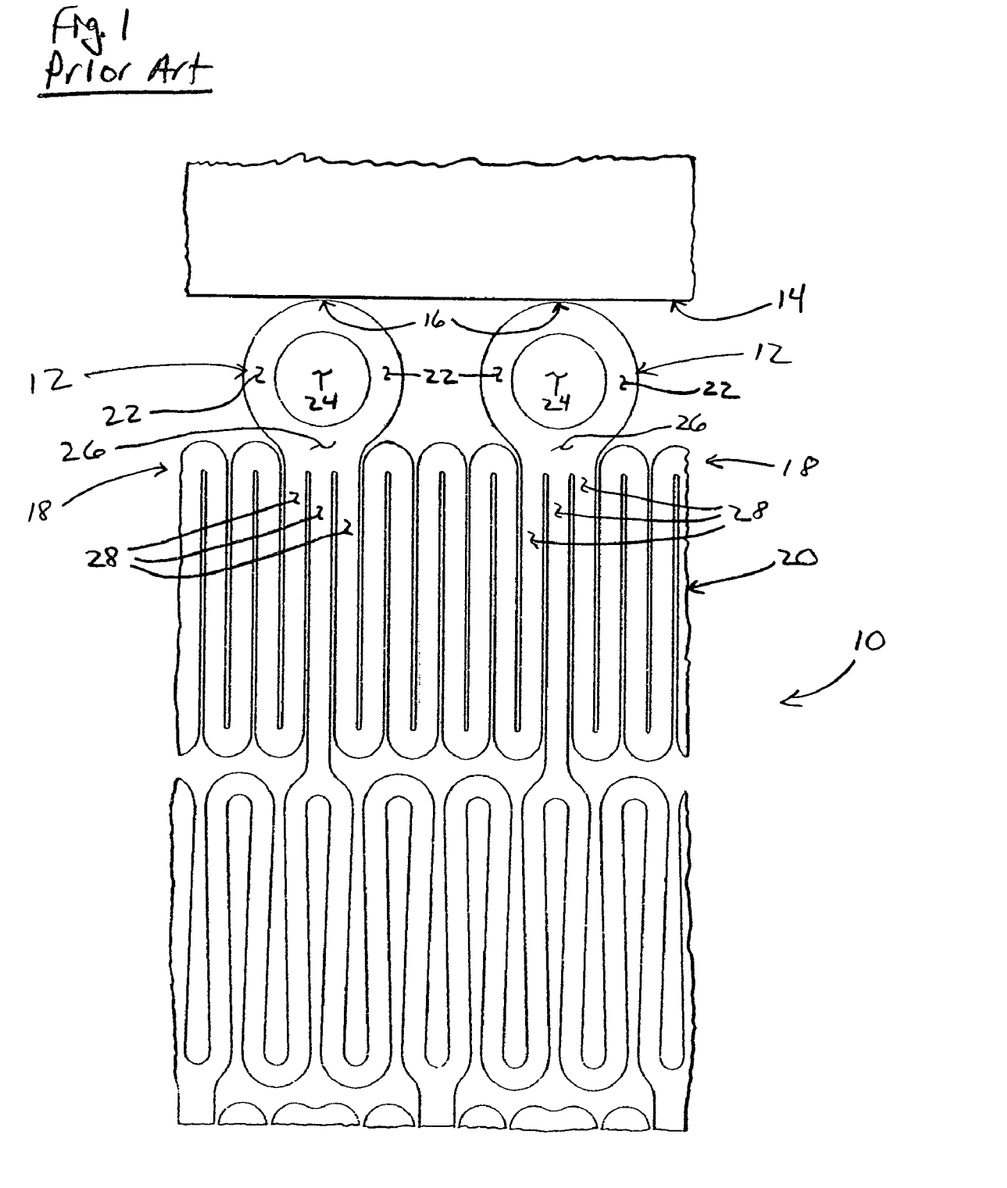
FIG. 1 is a top plan view of a portion of an end of a stent, showing a prior art marker configuration.

Referring now to the drawings, and particularly to FIG. 1, a stent 10 is shown with prior art markers 12. A holder 14 is also shown contacting the end surface 16 of the markers 12. The holder 14 that is shown is only intended to be representative of various types of holders that may be used to apply force to the end 16 of the markers 12. Typically, markers 12 like those shown are provided at both the proximal and distal ends 18 of the stent structure 20. The markers 12 are also usually equally spaced around the circumference of the stent 10. Commonly, four to eight markers 12 are provided at each end 18 of the stent 10. Normally, each of the markers 12 is formed integrally with the stent structure 20 and is defined by a ring 22 of the same material that the stent structure 20 is made from. A radial opening 24 is thus formed through the center of each of the markers 12. Usually, the radial opening 24 is filled with a rivet of radiopaque material, such as gold or platinum. As shown, the markers 12 are connected to the stent structure through a connecting portion 26.

One problem with prior art markers/pushing members like the one shown in FIG. 1 is that the markers 12 concentrate the pushing forces onto a relatively small area of the stent structure 20. Thus, for the stent 10 that is shown, all of the force that is transmitted through each of the markers 12 is concentrated on only those structural members 28 of the stent structure 20 that are directly connected to the connecting portion 26. As a result, the structural members 28 directly connected to the connecting portion 26 experience more pushing force than the rest of the stent structure 20. This may cause parts of the stent structure 20 to bend or deform as the holder 14 applies force to the markers 12.

Figure 2:
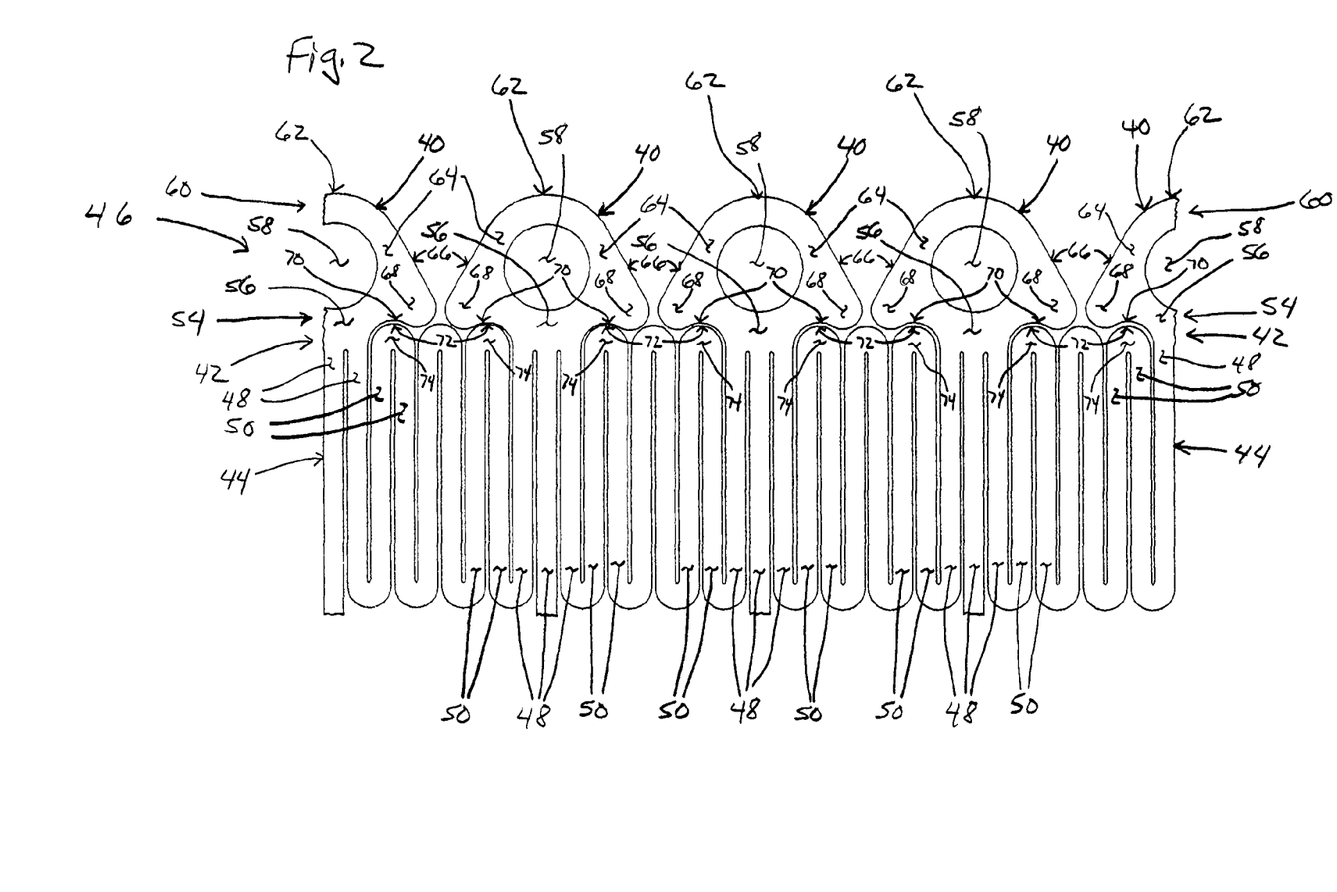
FIG. 2 is a top plan view of a portion of an end of a stent, showing markers with a rounded apex and lateral extensions.
Figure 4:
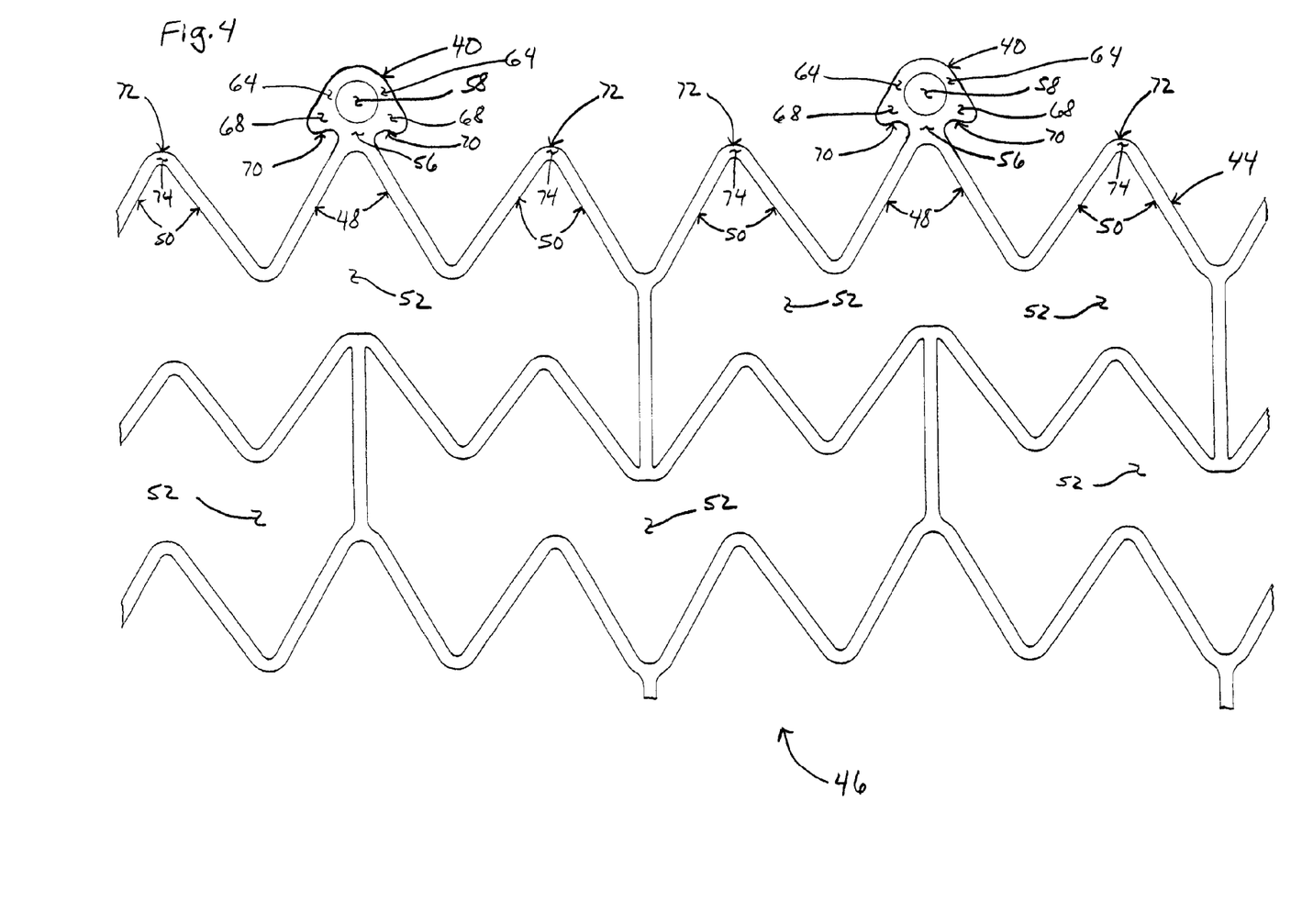
FIG. 4 is a top plan view of a portion of the stent shown in FIG. 2, showing the stent expanded.

Turning now to the other figures, a new marker/pushing member is shown. In FIGS. 2 and 4, one embodiment of a marker 40 is shown. The marker 40 is attached to or formed onto either a proximal or distal end 42 of a stent structure 44 or to both ends 42 of the stent structure 44. As those in the art know well, many types of stent structures are possible. In general, stent structures 44 may be made of a series of structural members, or struts, 48, 50 that define a generally cylindrical structure. Accordingly, the stent structure 44 typically has inner and outer surfaces and proximal and distal ends 42.

Generally, the stent 46 is designed to compress and expand. In FIG. 2, an example of a stent structure 44 in a compressed state is shown, while in FIG. 4 an example of the same stent structure 44 is shown in an expanded state. Radial compression and expansion is accomplished by providing a series of radial openings 52 that extend through the stent structure 44 between the inner and outer surfaces. Countless types of stent structures are known and/or are possible. For example, one type of stent structure is made by cutting the stent structure out of a metal cannula with a laser. In such a structure, all of the structural members, including the markers, are usually integrally interconnected since all of the stent features are cut from a single tube. However, other structures are also possible. For example, the stent structure may be a braided wire structure, in which individual wires are braided together in a fashion that permits the structure to compress and expand. In such a case, the markers could be integrally formed from the wires or could be separately attached to the structure.

As shown in FIG. 2, the marker 40 is attached along a first side 54 to the stent structure 44 through a connecting portion 56. In FIG. 2, three structural members 48 are directly connected to the connecting portion 56, while two structural members 48 are directly connected to the connecting portion 56 in FIG. 4. A radial opening 58 is provided through the center of the marker 40 so that radiopaque material may be inserted into the markers 40. The second side 60 of the marker 40 located away from the stent structure 44 provides the contact surface against which the holder applies a pushing force. In the case of FIGS. 2 and 4, the end surface 62 of the marker 40 is a rounded apex 62 centered about the radial opening 58. The first and second sides 54, 60 of the marker 40 are connected together by longitudinal members 64. In the case of the described embodiment, the longitudinal members 64 also define the sides of the radial opening 58. In the embodiment shown in FIGS. 2 and 4, the outer side surfaces of the longitudinal members 64 are angled from the longitudinal axis of the stent structure 44. The longitudinal members 64 and the connecting portion 56 are further connected to lateral extensions 68 on each side of the marker 40. The lateral extensions 68 extend along the first side 54 of the marker 40 adjacent the stent structure 44. Preferably, the side surfaces 70 of the lateral extensions 68 located adjacent the stent structure 44 are shaped with a rounded concave shape 70. This rounded concave shape 70 is designed to correspond to the rounded convex shape 72 of two structural members 50 where the members 50 are joined together along a joined portion 74. Thus, the potential contact area between the lateral extensions 68 and the joined portions 74 of the stent structure 44 is maximized by providing complementary shapes on both the lateral extensions 68 and the stent structure 44.

One of the advantages of the marker 40 is now apparent. Unlike prior art markers/pushing members which concentrate the pushing force onto a small number of the structural members in the stent structure, the described marker 40 distributes the pushing force over a wider area of the stent structure 44. Thus, whereas the prior art marker 12 shown in FIG. 1 concentrates the pushing force applied to each marker 12 on only three structural members 28 which are directly connected to the marker 12, the described marker 40 distributes the pushing force both to the structural members 48 directly connected to the marker 40 and also to other structural members 50 that are not directly connected to the marker 40. In the case of the embodiment described in FIG. 2, the marker 40 also distributes the pushing force through the lateral extensions 68 in addition to the connecting portion 56. As a result, part of the force is applied to the joined portions 74 of the structural members 50 located adjacent the connecting portion 56. Thus, the pushing force is shared by more of the structural members 48, 50 of the stent structure 44. Because the pushing force is spread out more evenly across the stent structure 44, less bending and deformation occurs to the stent structure 44 as it is pushed into the stent delivery system or as the stent 46 is released for implantation and pushed out of the stent delivery system. This is especially helpful when stents of longer length are used since these stents typically require higher pushing forces due to increased friction. As a result longer stents are typically more susceptible to bending and deformation than shorter stents. This is a more noticeable problem on stents that are longer than 8 cm.

Figure 3:
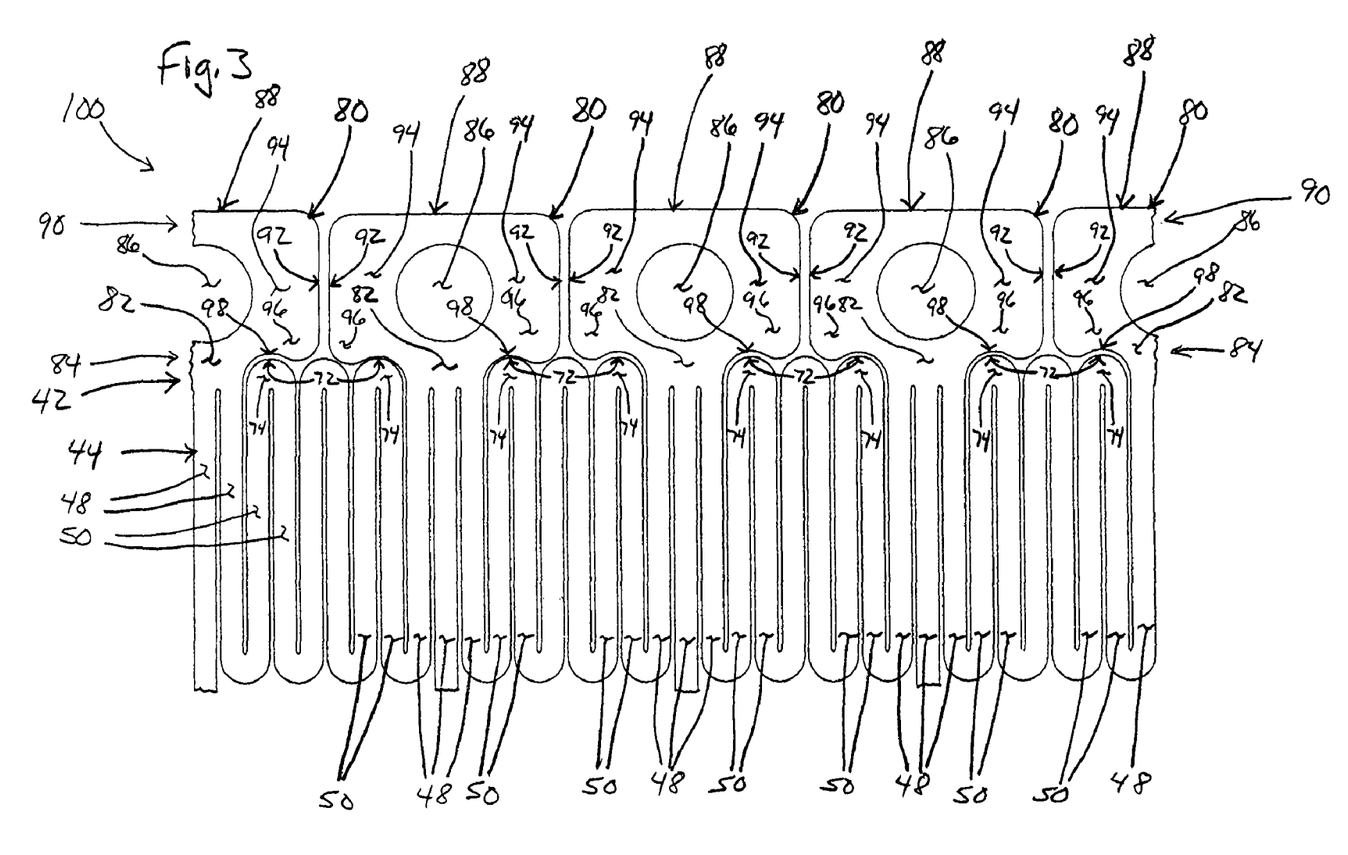
FIG. 3 is a top plan view of a portion of an end of a stent, showing markers with a flat end surface and lateral extensions.

In FIG. 3, another embodiment of the invention is shown. Like the previously described embodiment, the marker 80 is also attached to the stent structure 44 with a connecting portion 82 along the first side 84 of the marker 80. Similarly, a radial opening 86 is provided through the center of the marker 80. However, in this embodiment, the end surface 80 of the second side 90 of the marker 80 is flat 88 instead of rounded. Thus, the end surface 88 is parallel to the end 42 of the stent structure 44. The outer surfaces 92 of the longitudinal members 94 are also straight and extend generally parallel to the longitudinal axis of the stent structure 44. Like the previously described embodiment, the marker 80 in FIG. 3 is also provided with lateral extensions 96 extending outward from the connecting portion 82. Preferably, the side surfaces 98 of the lateral extensions 96 are shaped with a rounded concave shape 98 to complement the rounded convex shape 22 of the joined portion 74 of two structural members 50.

It is now apparent that the embodiment described in FIG. 3 offers similar advantages as described above. Like the embodiment shown in FIG. 2, this embodiment distributes the pushing force over a wider area of the stent structure 44. Also, like the previous embodiment, the larger markers 40, 80 may provide better visualization during implantation than prior markers. The embodiment shown in FIG. 3, however, provides straight side surfaces 92 on each of the markers 80, which may contact each other when the stent 100 is compressed. This may provide even more improved stability for the stent 100 as it is manipulated during various stages of use. This embodiment also provides a flat end surface 88 for contact with the holder.

Accordingly, it is now apparent that there are many advantages of the invention provided herein. In addition to the advantages that have been described, it is also possible that there are still other advantages that are not currently recognized but which may become apparent at a later time. For example, while the embodiments described herein have generally been described as relating to markers for a stent, it should also be kept in mind that the principles taught herein may also apply to pushing members that are not necessarily used for visualization purposes.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein.

I claim:

1. An expandable stent for medical implantation, comprising:
    a stent structure formed from a series of structural members, said stent structure being generally cylindrical with an inner surface, an outer surface, a proximal end, and a distal end, wherein a series of radial openings extend through said stent structure between said inner and outer surfaces thereby adapting said stent structure to expand from a compressed diameter to an expanded diameter, wherein said radial openings are defined by said series of structural members;
    a bend disposed at said at least one of said proximal and distal ends of said stent structure, said bend having an arc-shaped outer surface extending substantially 180 degrees between two of said structural members, wherein the bend comprises a uniform width substantially the same as a uniform width of said structural members, said bend being substantially closed when said stent structure is in said compressed diameter so that said two of said structural members are substantially parallel in said compressed diameter, and said bend being opened when said stent structure is in said expanded diameter so that said two of said structural members are angled away from each other in said expanded diameter; and
    a pushing member connected to at least one of said proximal and distal ends of said stent structure, said pushing member being connected along a first side of said pushing member through a connecting portion, said pushing member further comprising a second side disposed away from said first side and a longitudinal member connected to said first and second sides, whereby said second side is adapted to contact a holder and said longitudinal member is adapted to transmit force applied by said holder to said connecting portion and said stent structure,
    wherein said longitudinal member and said connecting portion are further connected to a lateral extension, said lateral extension being disposed along said first side and adjacent said stent structure, said lateral extension comprising a surface having a concave shape with respect to a laterally extending plane, said concave shape corresponding to said arc-shaped outer surface of said bend that extends substantially 180 degrees when said stent structure is in said compressed diameter, said surface of said lateral extension thereby being configured to directly receive substantially the entire arc-shaped outer surface of said bend that extends substantially 180 degrees when said stent is in said compressed diameter, whereby at least a portion of said force transmitted by said longitudinal member is distributed to said bend and said two of said structural members without substantially deforming structural members directly connected to said pushing member through said connecting portion.

2. The stent according to claim 1, wherein said pushing member comprises two of said longitudinal members and an opening extending radially through said pushing member, said opening being defined by said two longitudinal members and said first and second sides of said pushing member, said opening being filled with a radiopaque material, wherein said pushing member further comprises two of said lateral extensions disposed on opposite sides of said opening.

3. The stent according to claim 1, wherein said second side is rounded, an end surface of said pushing member thereby forming an apex away from said first side.

4. The stent according to claim 3, wherein a side surface of said longitudinal member extending between said apex and said lateral extension is angled from a longitudinal axis of said stent structure.

5. The stent according to claim 1, wherein said pushing member comprises two of said longitudinal members and an opening extending radially through said pushing member, said opening being defined by said two longitudinal members and said first and second sides of said pushing member, said opening being filled with a radiopaque material, and further comprising two of said lateral extensions disposed on opposite sides of said opening, said side surfaces of each of said two longitudinal members being angled from said longitudinal axis of said stent structure, wherein said apex is disposed along a centerline of said opening.

6. The stent according to claim 1, wherein said second side is flat, an end surface of said pushing member thereby extending parallel to said one of said proximal and distal ends.

7. The stent according to claim 6, wherein a side surface of said longitudinal member extending between said flat end surface and said lateral extension is generally parallel to a longitudinal axis of said stent structure.

8. The stent according to claim 7, wherein said pushing member comprises two of said longitudinal members and an opening extending radially through said pushing member, said opening being defined by said two longitudinal members and said first and second sides of said pushing member, said opening being filled with a radiopaque material, and further comprising two of said lateral extensions disposed on opposite sides of said opening, said side surfaces of each of said two longitudinal members being generally parallel to said longitudinal axis of said stent structure, wherein said opening is disposed along a centerline of said pushing member.

9. An expandable stent for medical implantation, comprising:
- a stent structure formed from a series of structural members, said stent structure being generally cylindrical with an inner surface, an outer surface, a proximal end, and a distal end, said structural members defining a series of radial openings extending through said stent structure between said inner and outer surfaces thereby adapting said stent structure to expand from a compressed diameter to an expanded diameter, wherein said radial openings are defined by said series of structural members;
- a bend disposed at said at least one of said proximal and distal ends of said stent structure, said bend having an arc-shaped outer surface extending substantially 180 degrees between two of said structural members, wherein the bend comprises a uniform width substantially the same as a uniform width of said structural members, said bend being substantially closed when said stent structure is in said compressed diameter so that said two of said structural members are substantially parallel in said compressed diameter, and said bend being opened when said stent structure is in said expanded diameter so that said two of said structural members are angled away from each other in said expanded diameter; and
- a pushing member connected to said one of said proximal and distal ends of said stent structure, said pushing member being connected along a first side of said pushing member through a connecting portion, said connecting portion being disposed adjacent said bend, said pushing member further comprising a second side disposed away from said first side, whereby said second side is adapted to contact a holder, a force applied by said holder being transmitted through said pushing member to said connecting portion and said stent structure,
- wherein said pushing member and said connecting portion are further connected to a lateral extension, said lateral extension being disposed along said first side and adjacent said connecting portion, said lateral extension comprising a surface having a concave shape with respect to a laterally extending plane, said concave shape corresponding to said arc-shaped outer surface of said bend that extends substantially 180 degrees when said stent structure is in said compressed diameter, said surface of said lateral extension thereby being configured to directly receive substantially the entire arc-shaped outer surface of said bend that extends substantially 180 degrees when said stent is in said compressed diameter, whereby at least a portion of said force transmitted through said pushing member is distributed away from said connecting portion and to said bend and said two of said structural members without substantially deforming structural members directly connected to said pushing member through said connecting portion.

10. The stent according to claim 9, wherein said second side of said pushing member is rounded with an end surface thereof forming an apex away from said first side, a side surface of said pushing member extending between said apex and said lateral extension thereby being angled from a longitudinal axis of said stent structure.

11. The stent according to claim 10, wherein said pushing member comprises an opening extending radially through said pushing member, said opening being defined by said first and second sides of said pushing member and two longitudinal members connecting said first and second sides, said opening being filled with a radiopaque material, and further comprising two of said lateral extensions disposed on opposite sides of said opening, side surfaces of each of said two longitudinal members being angled from said longitudinal axis of said stent structure, wherein said apex is disposed along a centerline of said opening.

12. The stent according to claim 9, wherein said second side of said pushing member is flat with an end surface thereof extending parallel to said one of said proximal and distal ends, a side surface of said pushing member extending between said flat end surface and said lateral extension thereby being generally parallel to a longitudinal axis of said stent structure.

13. The stent according to claim 12, wherein said pushing member comprises an opening extending radially through said pushing member, said opening being defined by said first and second sides of said pushing member and two longitudinal members connecting said first and second sides, said opening being filled with a radiopaque material, and further comprising two of said lateral extensions disposed on opposite sides of said opening, side surfaces of each of said two longitudinal members being generally parallel to said longitudinal axis of said stent structure, wherein said opening is disposed along a centerline of said pushing member.

14. An expandable stent for medical implantation, comprising:
- a stent structure formed from a series of structural members, said stent structure being generally cylindrical with an inner surface, an outer surface, a proximal end, and a distal end, wherein a series of radial openings extend through said stent structure between said inner and outer surfaces thereby adapting said stent structure to expand from a compressed diameter to an expanded diameter, wherein said radial openings are defined by said series of structural members;
- a bend disposed at said at least one of said proximal and distal ends of said stent structure, said bend having an arc-shaped outer surface extending substantially 180 degrees between two of said structural members, wherein the bend comprises a uniform width substantially the same as a uniform width of said structural members, said bend being substantially closed when said stent structure is in said compressed diameter so that said two of said structural members are substantially parallel in said compressed diameter, and said bend being opened when said stent structure is in said expanded diameter so that said two of said structural members are angled away from each other in said expanded diameter; and
- a marker connected to at least one of said proximal and distal ends of said stent structure, said marker being connected along a first side of said marker through a connecting portion, said marker further comprising a second side disposed away from said first side and side surfaces attaching said first and second sides,
- wherein said side surfaces and said connecting portion are further connected to lateral extensions extending circumferentially outward from said connecting portion, said lateral extensions being disposed along said first side and adjacent said stent structure, and said lateral extension comprising a surface having a concave shape with respect to a laterally extending plane, said concave shape corresponding to said arc-shaped outer surface of said bend that extends substantially 180 degrees when said stent structure is in said compressed diameter, said surface of said lateral extension thereby being configured to directly receive substantially the entire said arc-shaped outer surface of said bend that extends substantially 180 degrees when said stent is in said compressed diameter, whereby at least a portion of a force applied to said marker is transmitted through said connecting portion and distributed to said bend and said two of said structural members without substantially deforming structural members directly connected to said marker through said connecting portion.

15. The stent according to claim 14, wherein said side surfaces of said marker are angled from a longitudinal axis of said stent structure.

16. The stent according to claim 15, wherein said second side is rounded, an end surface of said marker thereby forming an apex away from said first side.

17. The stent according to claim 14, wherein said side surfaces of said marker are generally parallel to a longitudinal axis of said stent structure.

18. The stent according to claim 17, wherein said second side is flat, an end surface of said marker thereby extending parallel to said one of said proximal and distal ends.

* * * * *